(12) United States Patent
Yang et al.

(10) Patent No.: US 11,536,125 B1
(45) Date of Patent: Dec. 27, 2022

(54) METHOD FOR PROPPANT SUSPENSION AND SUSPENSION PARAMETER OPTIMIZATION BASED ON BUBBLE BRIDGE EFFECT

(71) Applicant: Chengdu University of Technology, Chengdu (CN)

(72) Inventors: Bin Yang, Chengdu (CN); Hao Zhang, Chengdu (CN); Yufan Guo, Chengdu (CN); Bo Yang, Chengdu (CN); Yin Zhong, Chengdu (CN); Yang Yang, Chengdu (CN); Wenjing Ma, Chengdu (CN); Yue Li, Chengdu (CN)

(73) Assignee: Chengdu University of Technology, Chengdu (CN)

( * ) Notice: Subject to any disclaimer, the term of this patent is extended or adjusted under 35 U.S.C. 154(b) by 0 days.

(21) Appl. No.: 17/844,301

(22) Filed: Jun. 20, 2022

(30) Foreign Application Priority Data

Oct. 20, 2021 (CN) .......................... 202111221578.6

(51) Int. Cl.
| | | |
|---|---|---|
| *E21B 43/267* | (2006.01) | |
| *B01F 23/231* | (2022.01) | |
| *B01F 23/50* | (2022.01) | |
| *E21B 43/26* | (2006.01) | |

(52) U.S. Cl.
CPC .......... *E21B 43/267* (2013.01); *B01F 23/231* (2022.01); *B01F 23/59* (2022.01); *E21B 43/2607* (2020.05)

(58) Field of Classification Search
None
See application file for complete search history.

(56) References Cited

U.S. PATENT DOCUMENTS

| | | | | |
|---|---|---|---|---|
| 2010/0252262 A1* | 10/2010 | Ekstrand | ............... | E21B 43/267 507/202 |
| 2014/0113841 A1* | 4/2014 | Shirley | .................. | C09K 8/703 507/202 |
| 2014/0318778 A1 | 10/2014 | Skala et al. | | |
| 2017/0183563 A1 | 6/2017 | Stanciu et al. | | |

(Continued)

FOREIGN PATENT DOCUMENTS

| | | |
|---|---|---|
| AU | 2015398683 A1 | 10/2017 |
| CN | 102781854 A | 11/2012 |

*Primary Examiner* — Andrew Sue-Ako
(74) *Attorney, Agent, or Firm* — Nitin Kaushik

(57) ABSTRACT

The present invention discloses a method for proppant suspension and suspension parameter optimization based on bubble bridge effect, comprising: select a proppant and hydrophobically modify its surface to obtain a hydrophobically surface-modified proppant; prepare a bubbly fracturing base fluid; make the first optimization of the base fluids according to the average radius of the proppant and the average radius of the bubbles of the base fluids; optimally select the base fluids selected for the second time according to the interaction energy between the proppant particle and the bubble after the hydrophobically surface-modified proppant mixed with the base fluid; the basic parameters of the bubbly fracturing base fluid selected at the third time were used for the perfect selection for proppant suspension. The present invention establishes a procedure on experimental evaluation and parameter calculation optimization by suspending fracturing proppant with the bubble bridge effect on the hydrophobic surface.

7 Claims, 12 Drawing Sheets

Schematic Diagram of Bubble Bridge Adsorbing and Connecting Proppant Particles to Form Aggregates

(56) References Cited

U.S. PATENT DOCUMENTS

2018/0362838 A1* 12/2018 Skiba .................. E21B 43/267
2019/0112521 A1   4/2019 McDaniel et al.
2019/0233715 A1   8/2019 Alexis et al.

* cited by examiner

Schematic Diagram of Bubble Bridge Adsorbing and Connecting Proppant Particles to Form Aggregates

METHOD FOR PROPPANT SUSPENSION AND SUSPENSION PARAMETER OPTIMIZATION BASED ON BUBBLE BRIDGE EFFECT

CROSS-REFERENCE TO RELATED APPLICATIONS

The application claims priority to Chinese patent application No. 202111221578.6, filed on Oct. 20, 2021, the entire contents of which are incorporated herein by reference.

TECHNICAL FIELD

The present invention relates to the technical field of stimulation for oil and gas reservoirs, in particular to a method for proppant suspension and suspension parameter optimization based on bubble bridge effect.

BACKGROUND

Hydraulic sand fracturing is one of the main stimulation measures for unconventional oil and gas reservoirs at present. In the fracturing process, proppant (ceramsite, quartz sand, etc.) is carried into the fractures by fracturing fluid to make the fractures remain open under the action of formation closing stress after the fracturing pump is stopped so as to achieve the purpose of stimulation by expanding the flow channels in oil and gas reservoirs. However, the density of proppant is often significantly higher than that of fracturing fluid, and the proppant will inevitably settle under the action of gravity, resulting in uneven distribution of proppant in the fracture. In other words, vertically the proppant concentration is high at the fracture bottom but very low or even no proppant at the top, and laterally it is high near the wellbore but very low or even no proppant at the far end of the fracture, imposing grave restraint effect to fracture opening and fracturing stimulation effect.

The existing methods for enhancing the proppant transportation effect by increasing the viscosity, viscoelasticity and pumping speed of fracturing fluid are disadvantaged by high material cost, strict requirements for pumping equipment and great risk of potential damage to reservoirs. With the continuous expansion of hydraulic fracturing scale, it is more and more difficult to meet the needs of field fracturing technologies. An alternative solution is to make it easier to carry proppant by reducing its density, for example, manufacture hollow ceramsite, low-density resin proppant, expanding polymer-coated proppant, etc. However, these methods are often not widely applied because of their high cost or high damage to the formation.

An air suspending agent for fracturing proppant and its construction method are disclosed in the prior art CN110724515A. Although it discloses a gas suspending agent for fracturing proppant, there is still a lack of feasible technical methods and guidance in related fields on how to use gas suspending agent to suspend the proppant and carry the proppant efficiently, how to determine fracturing fluid performance and indicator parameters according to proppant characteristics, and how to evaluate the stability of the fracturing base fluid-bubble-proppant suspension system, which greatly restricts the promotion and application of gas-based proppant suspension of fracturing fluid.

SUMMARY

In response to the above problems, the present invention is intended to provide a method for proppant suspension and suspension parameter optimization based on bubble bridge effect.

The technical solution of the present invention is as follows:

On the one and, the present invention provides a method for proppant suspension parameter optimization based on bubble bridge effect, comprising the following steps:

Select a proppant and measure its average particle size to obtain the average radius of the selected proppant;

Hydrophobically modify the surface of the selected proppant to obtain a hydrophobically surface-modified proppant;

Prepare the water-based fracturing base fluid, inject nitrogen into the base fluid, and stir it to cause uniform bubbles to obtain a bubbly fracturing base fluid;

Select a basic parameter of the bubbly water-based fracturing base fluid as a proppant suspension parameter for optimization, and prepare the bubbly water-based fracturing base fluid with different values of the basic parameter;

Measure the Zeta potential of the bubbly water-based fracturing base fluid with different basic parameter values, and take pictures of the bubbles of each base fluid with a high-speed camera to obtain the average radius of the bubbles of each base fluid by image analysis;

Make the first optimization of the base fluids according to the average radius of the proppant and the average radius of the bubbles of the base fluids;

Prepare an electrolyte solution with the same pH as that of each base fluid selected at the first time, put the hydrophobically surface-modified proppant into the electrolyte solution, and determine the Zeta potential of the hydrophobically surface-modified proppant in each electrolyte solution;

On the basis of the extended DLVO theory, calculate the interaction energy between the proppant particle and the bubble after the hydrophobically surface-modified proppant is mixed with the base fluids selected at the first time;

Optimally select the base fluids selected for the second time according to the interaction energy;

Put the hydrophobically surface-modified proppant into each base fluid selected at the second time and stir them; under the control of the interaction energy between the hydrophobic surface of the proppant and the bubble, the proppant particles are connected and aggregated through the bubble bridge effect; meanwhile, take pictures of the proppant-bubble-proppant aggregation with the high-speed camera, determine the coefficient of bonding ratio between the proppant particle and the bubble through image observation and statistical analysis, and calculate the apparent density of proppant-bubble aggregates;

Optimally select the base fluids selected for the third time according to the apparent density of proppant-bubble aggregates; the basic parameters of the bubbly fracturing base fluid selected at the third time were used for the perfect selection for proppant suspension.

Preferably, the proppant surface was hydrophobically modified by coating the proppant surface with an organic liquid suspending agent with hydrophobic effect.

Preferably, the organic liquid suspending agent was a hydrophobic resin with hydrophobic carbon chains.

Preferably, the basic parameters of the bubbly fracturing base fluid included pH value, salinity, Zeta potential, bubble size, amount of treating agent added, volume of gas injected.

Preferably, the first optimization of the base fluids included the following sub-step: calculate the ratio of the average radius of the proppant to the average radius of the bubbles of the base fluid; the base fluids with a ratio in the range of 0.5-2 were considered as the base fluids selected at the first time.

Preferably, the interaction energy between the proppant particle and the bubble includes Van der Waals interaction energy, repulsive potential energy of the electric double layer, hydrophobic interaction force, and hydration repulsive force.

Preferably, the interaction energy between the proppant particle and the bubble is calculated by the following equation:

$$\Phi_T = \Phi_{LVD} + \Phi_{EDL} + \Phi_{HA} + \Phi_{HR} \tag{1}$$

Where, $\Phi_T$ is the interaction energy between the proppant particle and the bubble, in J; $\Phi_{LVD}$ is the Van der Waals interaction energy between the proppant particle and the bubble, in J; $\Phi_{EDL}$ is the repulsive potential energy of the electric double layer between the proppant particle and the bubble, in J; $\Phi_{HA}$ is the hydrophobic interaction force between the proppant particle and the bubble, in J; $\Phi_{HR}$ is the hydration repulsive force between the proppant particle and the bubble, in J;

Where, the Van der Waals interaction energy is calculated by the following equation:

$$\Phi_{LVD} = -\frac{A_{132}}{6D}\left(\frac{R_1 R_2}{R_1 + R_2}\right) \tag{2}$$

Where, $A_{132}$ is the Hamaker constant of the interaction between the proppant particle and the bubble in the base fluid, in J; D is the interaction distance between the proppant particle surface and the bubble surface, in in; $R_1$ and $R_2$ are the average values of proppant particles and bubbles, respectively, in m;

The repulsive potential energy of the electric double layer is calculated by the following equation:

$$\Phi_{EDL} = \pi\varepsilon_r\varepsilon_0 \frac{R_1 R_2}{R_1 + R_2}\left\{2\zeta_1\zeta_2 \ln\left[\frac{1+\exp(-\kappa D)}{1-\exp(-\kappa D)}\right] + (\zeta_1^2 + \zeta_2^2)\ln[1-\exp(-2\kappa D)]\right\} \tag{3}$$

Where: $\varepsilon_r$ is the relative permittivity, taken as 81.5 for aqueous solution; $\varepsilon_0$ is the permittivity in vacuum, taken as $8.854\times10^{-12}$ CV$^{-1}$m$^{-1}$; $\zeta_1$ and $\zeta_2$ are the Zeta potentials of the proppant particle and the bubble, respectively, in V; $\kappa$ is the reciprocal value of the Debye length, in m$^{-1}$;

The hydrophobic interaction force is calculated by the following equation:

$$\Phi_{HA} = 2\pi \frac{R_1 R_2}{R_1 + R_2} h_{01} V_{HA}^0 \exp\left(-\frac{D}{h_{01}}\right) \tag{4}$$

Where, $h_{01}$ is the attenuation length of the hydrophobic interaction force, in m; $V^0_{HA}$ is the hydrophobic interaction energy constant between the proppant particle surface and the bubble, in J/m$^2$;

The hydration repulsive force is calculated by the following equation:

$$\Phi_{HR} = 2\pi \frac{R_1 R_2}{R_1 + R_2} h_{02} V_{HR}^0 \exp\left(-\frac{D}{h_{02}}\right) \tag{5}$$

Where, $h_{02}$ is the attenuation length of the hydration interaction force, in m; $V^0_{HR}$ is the hydration interaction energy constant between the proppant particle surface and the bubble, in J/m$^2$.

Preferably, optimally selecting the base fluids selected for the second time according to the interaction energy comprises the following steps: compare the interaction energy of each base fluid, wherein the base fluids with relatively stronger hydrophobic attraction between the proppant particle and the bubble were more conducive to the formation of stable proppant-bubble suspension aggregates, and the corresponding base fluids were considered as the base fluids selected at the second time.

Preferably, the apparent density of the proppant-bubble aggregates was calculated by the following equation:

$$\rho_a = \frac{\rho_1 R_1^3 + k\rho_2 R_2^3}{R_1^3 + kR_2^3} \tag{6}$$

Where, $\rho_a$ is the apparent density of proppant-bubble aggregates, in g/cm$^3$; $\rho_1$ is the density of proppant particles, in g/cm$^3$; k is the coefficient of bonding ratio between the proppant particle and the bubble in aggregates, causeless; $\rho_2$ is the density of the bubbles, in g/cm$^3$.

Preferably, the third optimization of base fluids selected at the second time was achieved by the following sub-step: sort out proppant-bubble aggregates with an apparent density in the range of 0.9-1.1 g/cm$^3$; the base fluids corresponding to the proppant-bubble aggregates were considered as the base fluids selected at the third time.

On the other hand, the present invention further provides a method for proppant suspension based on bubble bridge effect, comprising the following steps:

Select a proppant and hydrophobically modify its surface to obtain a hydrophobically surface-modified proppant;

Optimally select the suspension parameters of the proppant according to one of above methods for proppant suspension parameter optimization based on bubble ridge effect;

Prepare a bubbly water-based fracturing base fluid based on the results of the proppant suspension parameter optimization; and Mix the hydrophobically surface-modified proppant with the bubbly fracturing base fluid to obtain a proppant suspension fracturing fluid that forms a gas-liquid-solid mixed system.

The present invention has the following beneficial effects:

Based on the extended DLVO theory, the method for optimizing the proppant suspension parameters disclosed by the present invention is to establish a procedure on experimental evaluation and parameter calculation optimization by suspending fracturing proppant with the bubble bridge effect on the hydrophobic surface, which can optimize the apparent density of proppant and bubble aggregates by adjusting relevant parameters, ensuring efficient proppant suspension and transport under the conditions of different water-based fracturing fluid systems, proppant particle sizes and densities, fracturing pumping engineering parameters and reservoir characteristics, thereby achieving longer transport distance and more uniform displacement of fracturing proppant in both longitudinal and transverse directions, and significantly improving the hydraulic fracture stimulation effect of the reservoirs and the production of oil and gas wells.

The proppant suspension method stated in the present invention is to establish bubble bridges among the proppant particles under the mutual attraction between the hydrophobic surface of the proppant and the bubbles in the base fracturing fluid in order to form proppant-bubble aggregates, effectively reducing the apparent density of the aggregates as a whole, thereby achieving effective suspension of high-density proppant in the fracturing fluid.

BRIEF DESCRIPTION OF DRAWINGS

In order to explain the embodiments of the present invention or the technical solutions in the prior art more clearly, the following will make a brief introduction to the drawings needed in the description of the embodiments or the prior art. Obviously, the drawings in the following description are merely some embodiments of the present invention. For those of ordinary skill in the art, other drawings can be obtained based on the structures shown in these drawings without any creative effort.

DETAILED DESCRIPTION OF THE EMBODIMENTS

Figure 1:
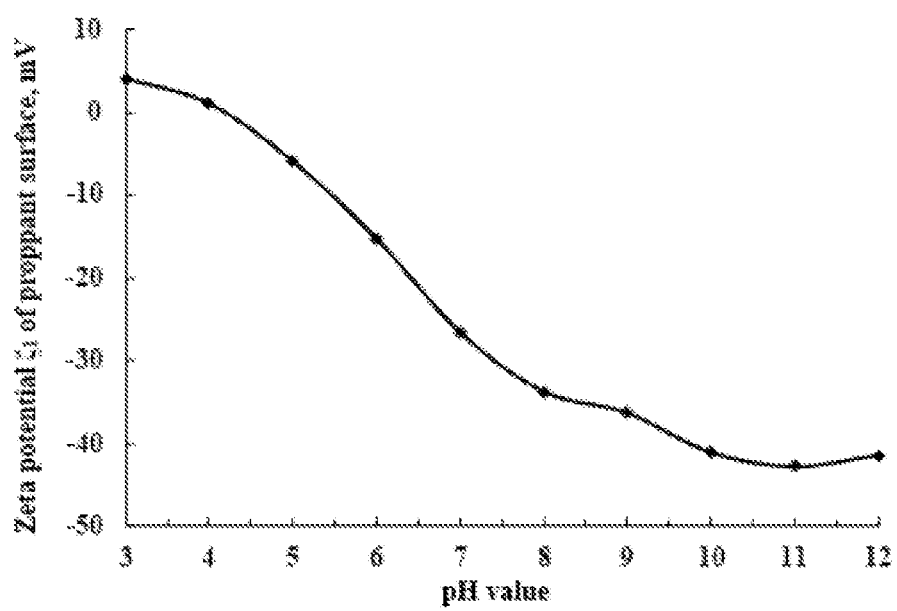
FIG. 1 is a schematic diagram on test result of Zeta potential of hydrophobic modified proppant surface in one embodiment.

The present invention is further described with reference to the drawings and embodiments. It should be noted that the embodiments in this application and the technical features in the embodiments can be combined with each other without conflict. It is to be noted that, unless otherwise specified, all technical and scientific terms herein have the same meaning as commonly understood by those of ordinary skill in the art to which this application belongs. "Include" or "comprise" and other similar words used in the present disclosure mean that the components or objects before the word cover the components or objects listed after the word and its equivalents, but do not exclude other components or objects.

On the one hand, the present invention provides a method for proppant suspension and suspension parameter optimization based on bubble bridge effect, comprising the following steps:

Step 1: Select a proppant and measure its average particle size to obtain the average radius of the selected proppant;

In a specific embodiment, the proppant was a commercially available fracturing proppant, specifically commercially available quartz sand, ceramsite, etc.

In a specific embodiment, a laser particle analyzer was employed to analyze the particle size of the selected proppant, and the proppant particle size covering 50% of the data points on the cumulative distribution curve of particle size was taken as the average particle size of the selected proppant;

Step 2: Hydrophobically modify the surface of the selected proppant to obtain a hydrophobically surface-modified proppant;

In a specific embodiment, the proppant surface was hydrophobically modified by coating the proppant surface with an organic liquid suspending agent with hydrophobic effect, and the organic liquid suspending agent was a hydrophobic resin with hydrophobic carbon chains;

Optionally, the organic liquid suspending agent can be the gas suspending agent for fracturing proppant disclosed in CN110724515A; the hydrophobic modification of the proppant surface with the organic liquid suspending agent specifically comprised the following sub-steps: select 30 pbw of commercially available proppant and 0.02-2 pbw of organic liquid suspending agent, dilute the organic liquid suspending agent with 10 pbw of fresh water, spray the solution on the proppant particle surface by atomization, stir the particles with a glass rod for 2-3 min to make the organic liquid suspending agent uniformly coated on the proppant surface, and the hydrophobic modification of the proppant surface will be realized after the organic liquid suspending agent is adsorbed;

It should be noted that the role of the organic liquid suspending agent is to hydrophobically modify the surface of the proppant, in addition to the organic liquid suspending agents applied in the above embodiments, other organic liquid suspending agents that can hydrophobically modify the surface of the proppant may also be applied to the present invention;

Step 3: Prepare the water-based fracturing base fluid, inject nitrogen into the base fluid, and stir it to cause uniform bubbles to obtain a bubbly fracturing base fluid;

In a specific embodiment, the water-based fracturing base fluid was composed of 0.05-0.1 pbw of a water-soluble hydrophobic viscosifier, 0.001-2 pbw of a foaming agent and 100 pbw of a solvent; Optionally, the water-soluble hydrophobic viscosifier can be an acrylamide associative polymer and/or modified guar gum, and the solvent can be water;

What needs illustration is that, in the above embodiments, the foaming agent is used in the prior art, and could be a commercially available non-ionic or ionic foaming agent as required; in addition to the water-soluble hydrophobic viscosifier and the solvent used in the above embodiments, other water-soluble hydrophobic viscosifiers and solvents in the prior art can also be adopted; furthermore, in addition to the water-based fracturing base fluid formulation used in the above embodiments, the present invention can also employ other water-based fracturing base fluids in the prior art, which can be prepared according to the actual fracturing conditions.

Step 4: Select a basic parameter of the bubbly water-based fracturing base fluid as a proppant suspension parameter for optimization, and repeat Step 3 to prepare the bubbly water-based fracturing base fluid with different values of the basic parameter;

In a specific embodiment, the basic parameters of the bubbly fracturing base fluid included pH value, salinity, Zeta potential, bubble size, amount of treating agent added, volume of gas injected, and the like; it should be noted that some base parameters may be interrelated; in other word, if one basic parameter is changed, other related parameters will also be changed accordingly, for example, if the amount of treating agent added is different, the Zeta potential and the bubble size will also be different, resulting in different suspension effect; when the present invention is implemented for optimization, one of the basic parameters is selected as a variable, and the optimal proppant suspension parameters can be determined through orthogonal experiments and other methods;

Step 5: Measure the Zeta potential of the bubbly water-based fracturing base fluid with different basic parameter values, and take pictures of the bubbles of each base fluid with a high-speed camera to obtain the average radius of the bubbles of each base fluid by image analysis;

In a specific embodiment, the zeta potential on the bubble surface was measured by sedimentation potential method; it should be noted that the technology of obtaining the average radius of the bubbles through image analysis is in the prior art, and the specific steps will not be described herein;

Step 6: Make the first optimization of the base fluids according to the average radius of the proppant and the average radius of the bubbles of the base fluids;

In a specific embodiment, the first optimization of the base fluids included the following sub-step: calculate the ratio of the average radius of the proppant to the average radius of the bubbles of the base fluid; the base fluids with a ratio in the range of 0.5-2 were considered as the base fluids selected at the first time; the ratio selected in the present invention can not only meet the demand for proppant suspension, but also avoid excessive bubbles and increase the friction of the system;

Step 7: Prepare an electrolyte solution with the same pH as that of each base fluid selected at the first time, put the hydrophobically surface-modified proppant into the electrolyte solution, and determine the Zeta potential of the hydrophobically surface-modified proppant in each electrolyte solution;

In a specific embodiment, the Zeta potential of the hydrophobically surface-modified proppant was tested and calculated with a micro-electrophoresis instrument;

Step 8: On the basis of the extended DLVO theory, calculate the interaction energy between the proppant particle and the bubble after the hydrophobically surface-modified proppant is mixed with the base fluids selected at the first time; the interaction energy includes Van der Waals interaction energy, repulsive potential energy of the electric double layer, hydrophobic interaction force, and hydration repulsive force;

In a specific embodiment, the interaction energy between the proppant particle and the bubble is calculated by the following equation:

$$\Phi_T = \Phi_{LVD} + \Phi_{EDL} + \Phi_{HA} + \Phi_{HR} \tag{1}$$

Where, $\Phi_T$ is the interaction energy between the proppant particle and the bubble, in J; $\Phi_{LVD}$ is the Van der Waals interaction energy between the proppant particle and the bubble, in J; $\Phi_{EDL}$ is the repulsive potential energy of the electric double layer between the proppant particle and the bubble, in J; $\Phi_{HA}$ is the hydrophobic interaction force between the proppant particle and the bubble, in J; $\Phi_{HR}$ is the hydration repulsive force between the proppant particle and the bubble, in J;

Where, the Van der Waals interaction energy is calculated by the following equation:

$$\Phi_{LVD} = -\frac{A_{132}}{6D}\left(\frac{R_1 R_2}{R_1 + R_2}\right) \tag{2}$$

Where, $A_{132}$ is the Hamaker constant of the interaction between the proppant particle and the bubble in the base fluid, in J; D is the interaction distance between the proppant particle surface and the bubble surface, in m; $R_1$ and $R_2$ are the average values of proppant particles and bubbles, respectively, in m;

The repulsive potential energy of the electric double layer is calculated by the following equation:

$$\Phi_{EDL} = \pi \varepsilon_r \varepsilon_0 \frac{R_1 R_2}{R_1 + R_2}\left\{2\zeta_1\zeta_2\ln\left[\frac{1+\exp(-\kappa D)}{1-\exp(-\kappa D)}\right] + (\zeta_1^2 + \zeta_2^2)\ln[1-\exp(-2\kappa D)]\right\} \tag{3}$$

Where: $\varepsilon_r$ is the relative permittivity, taken as 81.5 for aqueous solution; $\varepsilon E_0$ is the permittivity in vacuum, taken as $8.854\times10^{-12}$ $CV^{-1}m^{-1}$, $\zeta_1$ and $\zeta_2$ are the Zeta potentials of the proppant particle and the bubble, respectively, in V; $\kappa$ is the reciprocal value of the Debye length, in $m^{-1}$;

The hydrophobic interaction force is calculated by the following equation:

$$\Phi_{HA} = 2\pi \frac{R_1 R_2}{R_1 + R_2} h_{01} V_{HA}^0 \exp\left(-\frac{D}{h_{01}}\right) \tag{4}$$

Where, $h_{01}$ is the attenuation length of the hydrophobic interaction force, in m; $V^O_{HA}$ is the hydrophobic interaction energy constant between the proppant particle surface and the bubble, in $J/m^2$;

The hydration repulsive force is calculated by the following equation:

$$\Phi_{HR} = 2\pi \frac{R_1 R_2}{R_1 + R_2} h_{02} V_{HR}^0 \exp\left(-\frac{D}{h_{02}}\right) \tag{5}$$

Where, $h_{02}$ is the attenuation length of the hydration interaction force, in m; $V^O_{HR}$ is the hydration interaction energy constant between the proppant particle surface and the bubble, in $J/m^2$;

In a specific embodiment, the hydrophobic interaction energy constant between the proppant particle surface and the bubble and the hydration interaction energy constant between the proppant particle surface and the bubble were tested and obtained with atomic force microscope;

Step 9: Optimally select the base fluids selected for the second time according to the interaction energy; specifically, compare the interaction energy of each base fluid, wherein the base fluids with relatively stronger hydrophobic attraction between the proppant particle and the bubble were more conducive to the formation of stable proppant-bubble suspension aggregates, and the corresponding base fluids were considered as the base fluids selected at the second time;

Step 10: Put the hydrophobically surface-modified proppant into each base fluid selected at the second time and stir them; under the control of the interaction energy between the hydrophobic surface of the proppant and the bubble, the proppant particles are connected and aggregated through the bubble bridge effect; meanwhile, take pictures of the proppant-bubble-proppant aggregation with the high-speed camera, determine the coefficient of bonding ratio between the proppant particle and the bubble through image observation and statistical analysis, and calculate the apparent density of proppant-bubble aggregates;

In a specific embodiment, the apparent density of the proppant-bubble aggregates was calculated by the following equation:

$$\rho_a = \frac{\rho_1 R_1^3 + k\rho_2 R_2^3}{R_1^3 + kR_2^3} \quad (6)$$

Where, $\rho_a$ is the apparent density of proppant-bubble aggregates, in $g/cm^3$; $\rho_1$ is the density of proppant particles, in $g/cm^3$; $\kappa$ is the coefficient of bonding ratio between the proppant particle and the bubble in aggregates, causeless; $\rho_2$ is the density of the bubbles, in $g/cm^3$.

To be sure, it is a prior art to determine the coefficient of bonding ratio between the proppant particle and the bubble through image observation and statistical analysis, and the specific steps will not be described herein;

Step 11: Optimally select the base fluids selected for the third time according to the apparent density of proppant-bubble aggregates; the basic parameters of the bubbly fracturing base fluid selected at the third time were used for the perfect selection for proppant suspension;

In a specific embodiment, the third optimization of base fluids selected at the second time was achieved by the following sub-step: sort out proppant-bubble aggregates with an apparent density in the range of 0.9-1.1 $g/cm^3$; the base fluids corresponding to the proppant-bubble aggregates were considered as the base fluids selected at the third time;

It is important that in the above embodiment, the base fluid with an apparent density in the range of 0.9-1.1 $g/cm^3$ was selected because the density was similar to that of the conventional water-based fracturing fluid (1.0-1.05 $g/cm^3$), which can achieve better proppant suspension effect; when the density of the water-based fracturing fluid is changed, the apparent density of the proppant-bubble aggregates will also be changed; specifically in the third optimization, select the base fluid corresponding to the proppant-bubble aggregates whose apparent density is closer to the density of water-based fracturing fluid to achieve the better suspension effect.

It should be noted that, when the base fluid is selected for the third time, if the apparent density of the proppant-bubble aggregates prepared is less than 0.9 $g/cm^3$ or greater than 1.1 $g/cm^3$, it is necessary to return to Step 3 to adjust the parameters of the system, such as the amount of foaming agent added, pH value and the amount of injected nitrogen, to make the apparent density of proppant-bubble aggregates fall in the limit range of 0.9-1.1 $g/cm^3$, and take the amount of treating agent as the final system formulation.

On the other hand, the present invention also provides a method for proppant suspension based on bubble bridge effect, comprising the following steps:

Select a proppant and hydrophobically modify its surface to obtain a hydrophobically surface-modified proppant;

Optimally select the suspension parameters of the proppant according to one of above methods for proppant suspension parameter optimization based on bubble ridge effect;

Prepare a bubbly water-based fracturing base fluid based on the results of the proppant suspension parameter optimization; and Mix the hydrophobically surface-modified proppant with the bubbly fracturing base fluid to obtain a proppant suspension fracturing fluid that forms a gas-liquid-solid mixed system.

Figure 2:
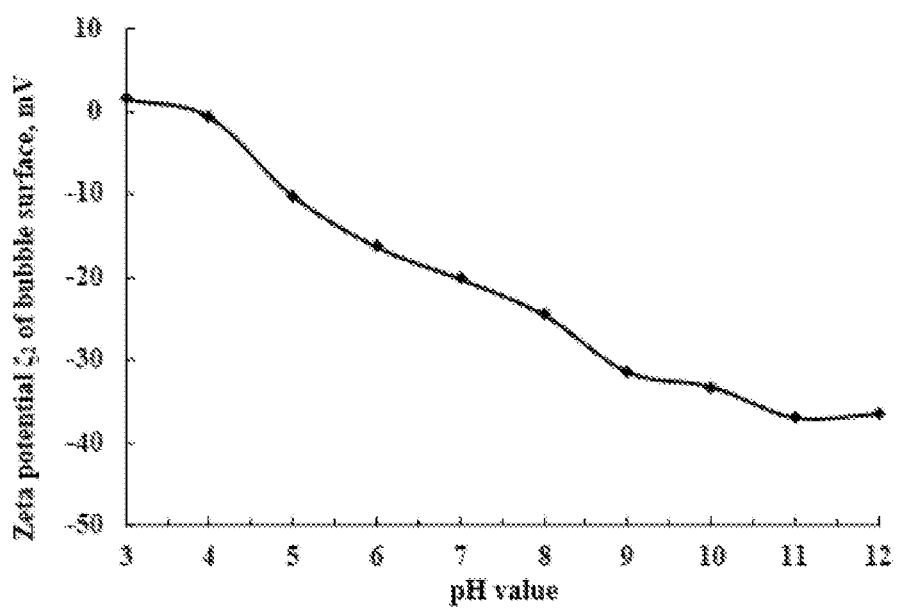
FIG. 2 is a schematic diagram on test results of Zeta potential on bubble surface of each bubbly fracturing base fluid in one embodiment.
Figure 3:
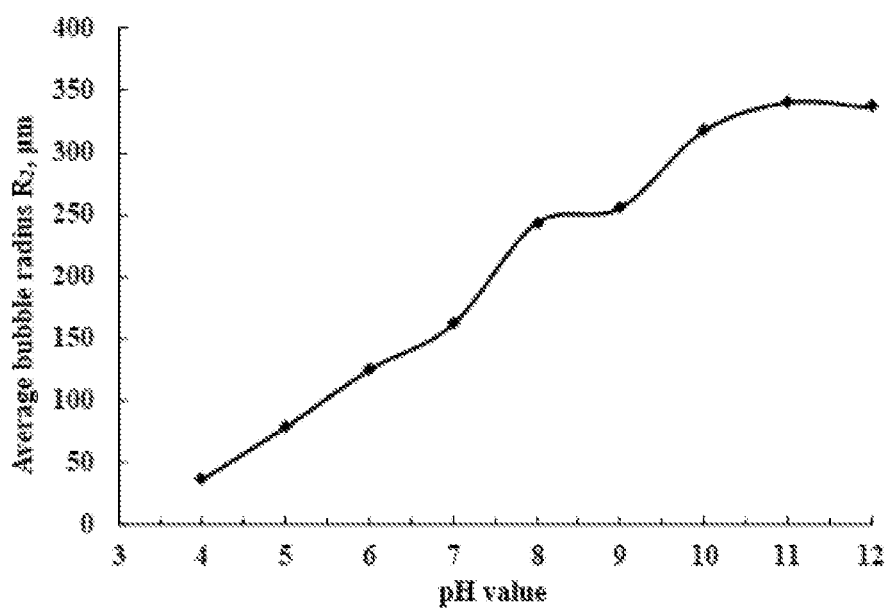
FIG. 3 is a schematic diagram on test results of average bubble radius of each bubbly fracturing base fluid with different pH values in one embodiment.
Figure 4:
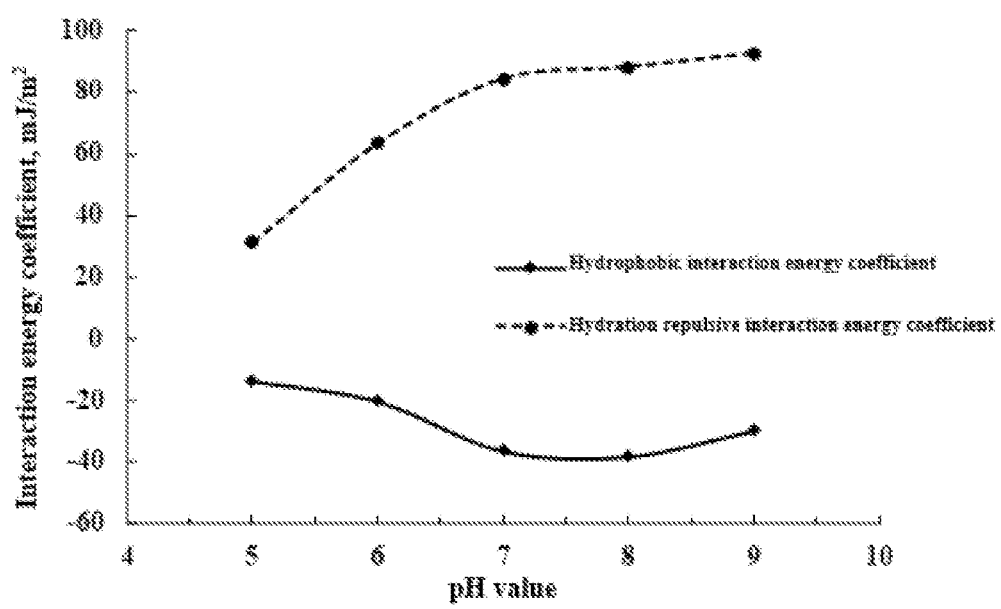
FIG. 4 is a schematic diagram on test result of interaction energy constants of each bubbly fracturing base fluid firstly optimized in one embodiment.
Figure 5:
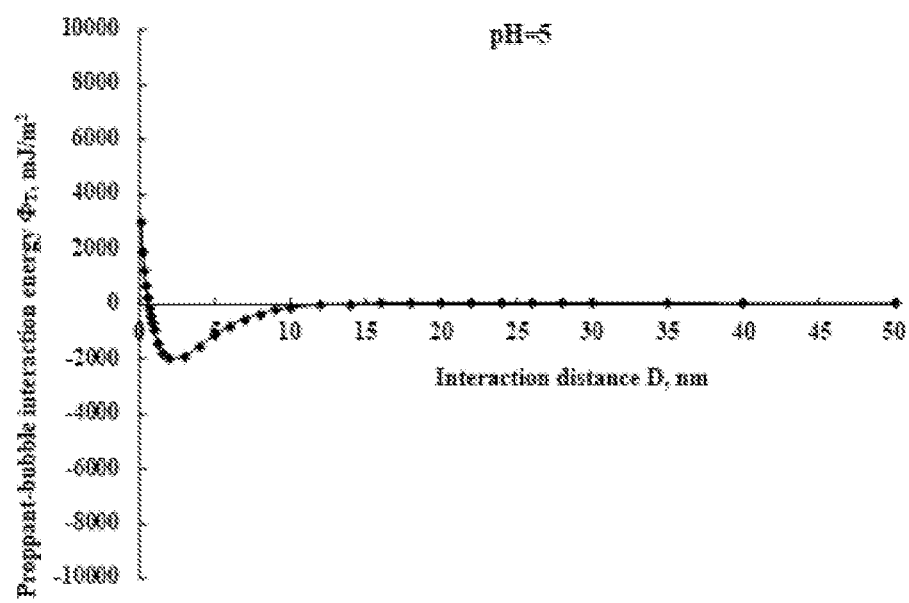
FIG. 5 is a schematic diagram on calculation results of interaction energy at pH=5 in one embodiment.
Figure 6:
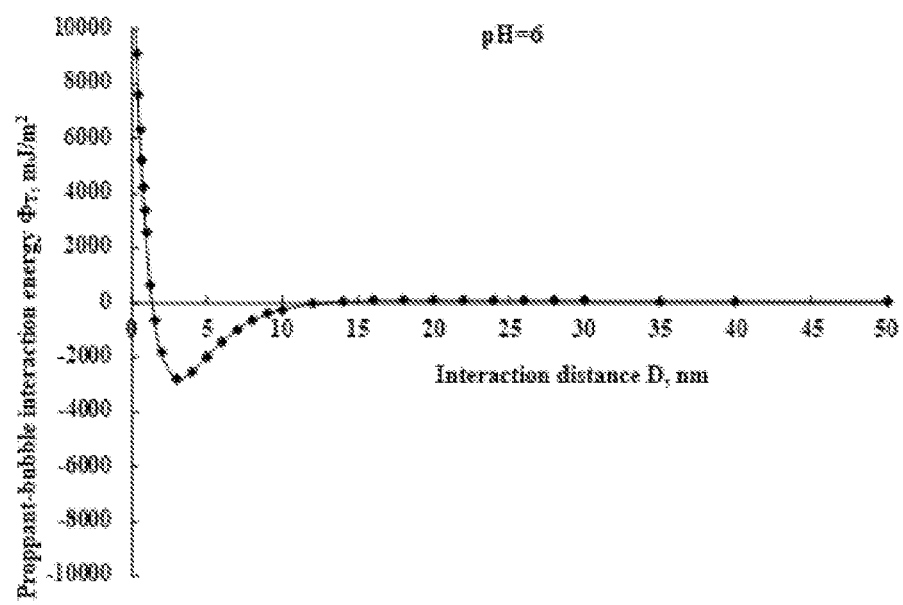
FIG. 6 is a schematic diagram on calculation results of interaction energy at pH=6 in one embodiment.
Figure 7:
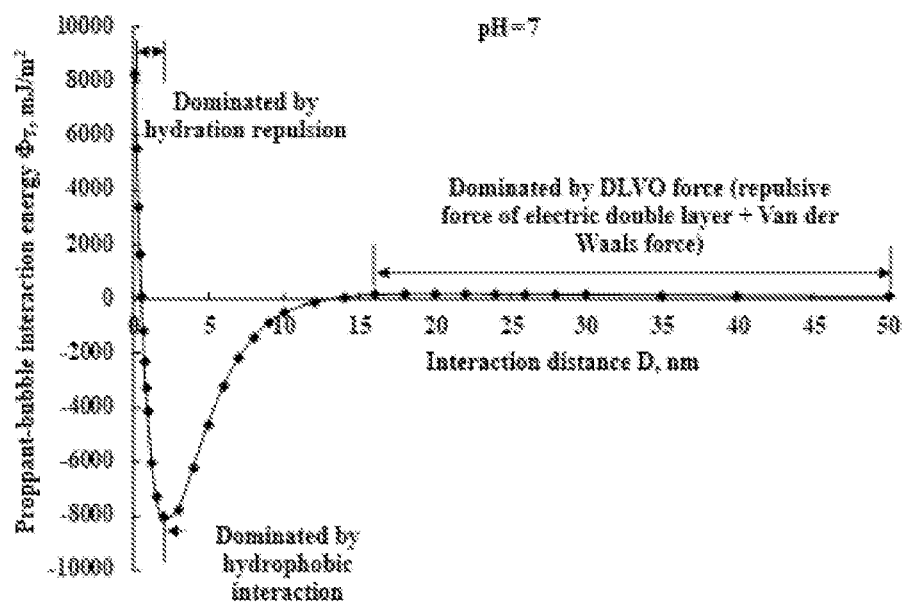
FIG. 7 is a schematic diagram on calculation results of interaction energy at pH=7 in one embodiment.
Figure 8:
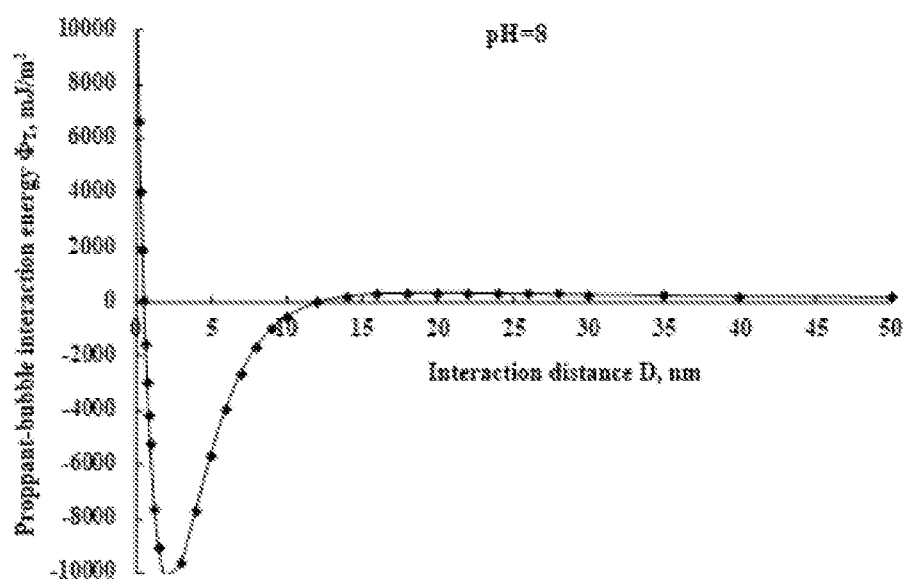
FIG. 8 is a schematic diagram on calculation results of interaction energy at pH=8 in one embodiment.
Figure 9:
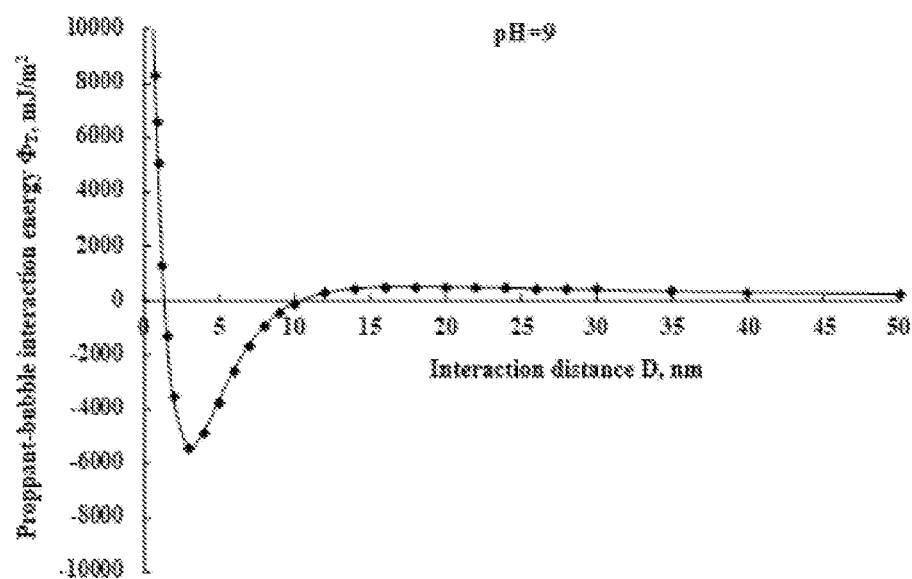
FIG. 9 is a schematic diagram on calculation results of interaction energy at pH=9 in one embodiment.
Figure 10:
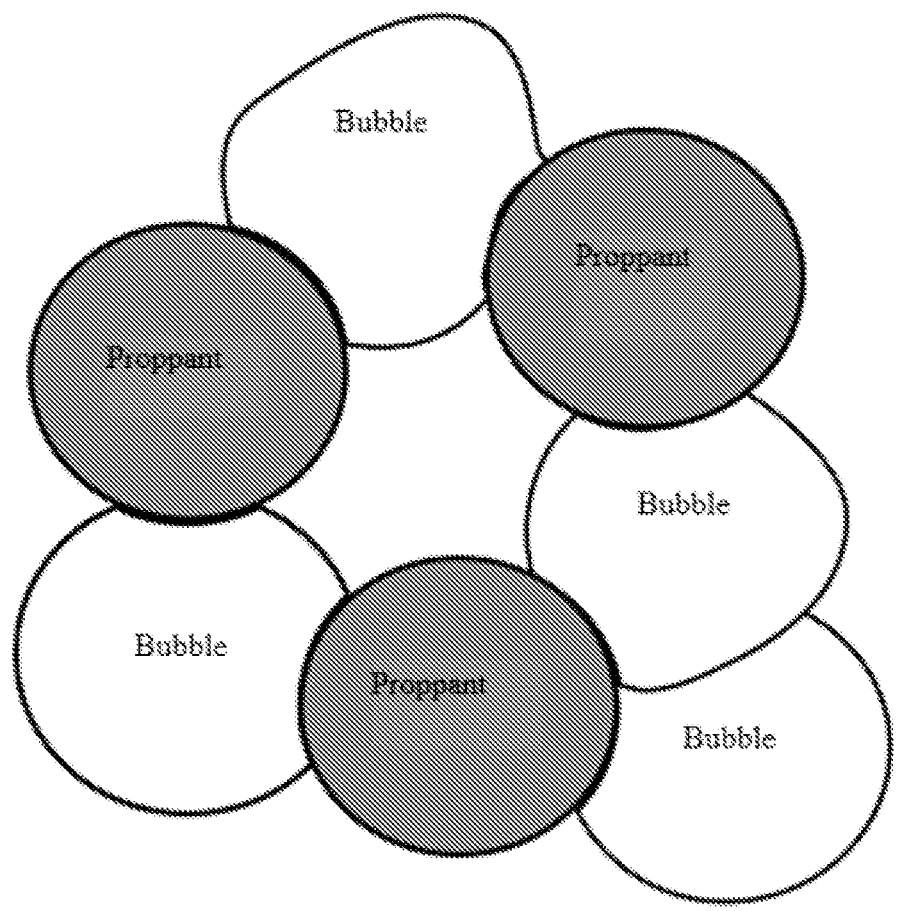
FIG. 10 is a structural diagram on bubble bridge adsorbing and connecting proppant particles to form aggregates.
Figure 11:
FIG. 11 is a schematic diagram on proppant suspension results of each bubbly fracturing base fluid secondly optimized in one embodiment.

In a specific embodiment, the pH value of the base fluid is used as the proppant suspension parameter for the optimization in the present invention, which specifically comprises the following steps:

(1) Select a quartz sand proppant for hydraulic fracturing for oil and gas well stimulation sold in Gongyi City, Henan Province, with a bulk density ($\rho_1$) of 2.68 $g/cm^3$ and a size of 40-70 mesh; measure the particle size (diameter) distribution ($D_{10}$=225.4 μm, $D_{50}$=312.6 μm and $D_{90}$=371.8 μm) of the proppant with Malvern laser sizer and take the $D_{50}$ value as the average particle size of the proppant sample to work out the average radius ($R_1$=156.3 μm) of the proppant particles;

(2) Weigh 30 pbw of the above proppant, dilute 0.1 pbw of organic liquid suspending agent (the gas suspending agent stated in CN110724515A) with pbw of fresh water, spray it onto the proppant particle surfaces by atomization, stir the auxiliary suspending agent with a glass rod for 2-3 min to make it evenly coated on the proppant surface, and the hydrophobic modification of the proppant surface will be realized after the suspending agent is adsorbed;

(3) Weigh 30 pbw of the hydrophobically surface-modified quartz sand proppant, put it into 100 pbw of 2% NaCl aqueous solution, stir them evenly, and then adjust the pH of the electrolyte solution with HCl and NaOH; further, adjust the pH value of the solution to be 3, 4, 5, 6, 7, 8, 9, 10, 11 and 12, take samples at each pH value, and test the Zeta potential ($\zeta_1$) of the hydrophobically modified proppant with Brookhaven micro-electrophoresis instrument (Zeta-PALS), with the results shown in FIG. 1;

(4) Prepare the fracturing base fluid required for proppant suspension, specifically composing 0.05 pbw of water-soluble hydrophobic viscosifier (GAF-TP produced by Sichuan Guangya Polymer Chemical Co., Ltd.), 0.02 pbw of ionic foaming agent and 100 pbw of fresh water; firstly drop the foaming agent into the water, stir it continuously while adding GAF-TP slowly to dissolve and disperse it, fully stir them to obtain a fracturing base fluid with a certain viscosity; the measure density ($\rho_0$) of the base fluid is 1.016 $g/cm^3$ and the viscosity of the base fluid measured by HAAKE rheometer is 6.42 mPa·s;

(5) Take 100 pbw of the fracturing base fluid prepared in Step (4) and adjust the pH value of the system with HCl and NaOH to make the pH value of each base fluid reach 3, 4, 5, 6, 7, 8, 9, 10, 11 and 12, then inject 5 pbw of nitrogen gas into the system, and stir the fluid with Waring mixer at a speed of 2,000 rpm to generate bubbles in the fracturing base fluid;

(6) Take samples from the base fluid of each pH value, determine the Zeta potential ($\zeta_2$) on the surface of the bubbles with the sedimentation potential method, with the results shown in FIG. 2; take pictures of the bubbles with CCD high-speed camera, and determine the bubble size with ImageJ software through gray scale identification; in this embodiment, if pH=3, no bubble was observed in the fracturing base fluid; if pH=4 to 12, the average radius ($R_2$) of the observed bubble was 37.4 to 268.3 μm; the specific test results are shown in FIG. 3;

(7) Calculate the ratio ($R_1/R_2$) between the average radius of the proppant obtained in Step (1) and the average radius of the bubbles obtained in Step (6), and control the ratio within the range of 0.5-2; when pH=5, 6, 7, 8 and 9, the bubble size meets the requirement;

(8) Test the interaction force curves between the hydrophobically surface-modified proppant and the base fluid bubble with atomic force microscope (AFM) under the conditions of pH=5, 6, 7, 8 and 9 respectively; fit the curves to obtain the hydrophobic interaction energy constant VO HA and the hydration interaction energy constant VO HR between the proppant surface and the bubble at different pH values, as shown in FIG. 4;

(9) According to the basic parameters measured in Steps (1) to (8), calculate the interaction energy between the surface of the hydrophobic modified proppant particle and the bubbles with different pH values by Equations (1) to (5); the curves of total interaction intensity are shown in FIGS. 5 to 9;

(10) According to the test results in FIGS. 5 to 9, optimally select the base fluids with pH=5, 6, 7, 8 and 9 for the second time, specifically:

Taking the proppant-bubble interaction curve at pH=7 as an example, when the distance between the proppant particle surface and the bubble is long, the interaction between them is dominated by the repulsive force of electric double layer and Van der Waals interaction force, and the interaction energy constant is positive, indicating that there is a weak repulsion between them; under the action of external forces such as stirring, when the distance between the proppant and the bubble is further reduced, the interaction energy between the proppant surface and the bubble turns to be negative under the action of hydrophobic effect, indicating that there is an attractive interaction between them, and as the distance decreases, the attractive force is further increased; under the attractive interaction, the proppant particles and bubbles are adsorbed stably, macroscopically forming proppant particle-bubble aggregates and making the proppant suspending by apparent density reduction; as the distance is decreased to the thickness of several water molecule layers, the hydration repulsive force begins to play a dominant role, preventing the proppant from further approaching the bubbles, which is macroscopically beneficial to inhibit the proppant-bubble aggregates from growing too big, while maintaining the stability of the system;

At pH=5-9, the hydrophobic interaction between the proppant particle and the bubble first increases and then decreases as the pH increases, and the extreme value of attractive force (negative value) in the range dominated by hydrophobic interaction is increased from $-1,994.6 \times 10^{-18}$ $J/m^2$ to $-10,058.7 \times 10^{-18}$ $J/m^2$, and then decreased to $-5,428.5 \times 10^{18}$ $J/m^2$; according to FIG. 5 to FIG. 9, at pH=7 or 8, the hydrophobic attractive force between the proppant and the bubble is the strongest relatively, which is most favorable for the formation of stable proppant-bubble suspension aggregates, therefore, a pH of 7 or 8 is preferred for the system;

(11) Prepare 200 pbw of the same fracturing base fluid as in step (4), and divide them equally into Groups A and B, and adjust the pH values of the base fluids in the two groups to 7 and 8 respectively according to the optimization results in Step (10); add 30 pbw of the hydrophobically surface-modified quartz sand proppant to the base fluids of Groups A and B, inject 5 pbw of nitrogen into each group, and stir them for 1 min at a speed of 2,000 rpm in Waring mixer; under the control of hydrophobic interaction between the proppant and the bubble, the proppant particles will bond and aggregate through the bubble bridge as shown in FIG. 10; take HD photos of the proppant particle-bubble aggregates in Groups A and B respectively with the CCD high-speed camera, and then apply the ImageJ software to gray scale identification and statistical analysis to obtain the coefficient κ of bonding ratio between the proppant particle and the bubble; the $\kappa_A$ was 1.46-1.59 for Group A (that is, one proppant particle bonding 1.46-1.59 bubbles) and $\kappa_B$ was 0.65-0.89 for Group B; the bubble radius in Group B was larger, the hydrophobic interaction was stronger, and single bubble could adsorb more particles, so its coefficient of bonding ratio was on the contrary lower;

(12) Given the known proppant particle radius ($R_1$) and bubble radius ($R_2$) at different pH values, considering that this embodiment was conducted at normal temperature and pressure, the bubble density ($\rho_2$) can be assumed to be 0 compared to the proppant density ($\rho_1$=2.68 $g/cm^3$); according to Equation (6), the apparent density of the proppant-bubble aggregates in Groups A and B of this embodiment can be calculated to be 0.962 to 1.014 $g/cm^3$ and 0.611 to 0.772 $g/cm^3$; the density of the fracturing base fluid in this example is 1.016 $g/cm^3$, which is close to that of Group A and much higher than the apparent density of Group B; the low density of proppant-bubble aggregates may lead to the proppant accumulation on the upper part of the fluid, which is not conducive to efficient sanding, so that Group A at pH=7 is determined as the preferred group in this embodiment; In addition, the suspension results of Groups A and B are shown in FIG. 11. It can be seen from FIG. 11 that the proppant of Group A is suspending while the proppant of Group B is floating completely.

Figure 12:
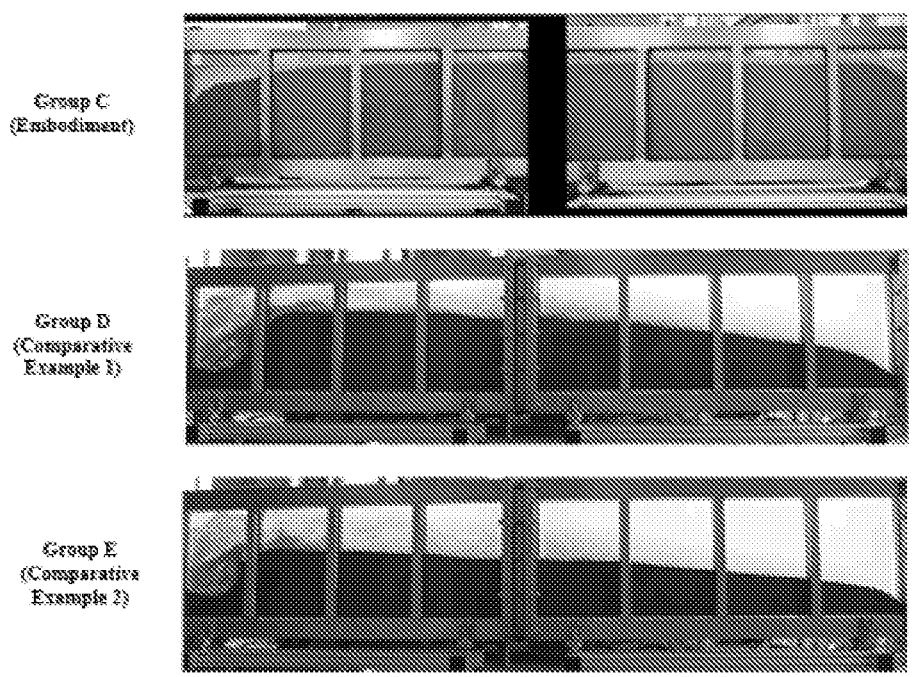
FIG. 12 is a schematic diagram on comparative test results of proppant-carrying effect between the present invention and conventional fracturing fluid.

According to the optimization results of the above steps, prepare 3 $m^3$ of gas-carrying fracturing fluid (hydrophobically modified quartz sand proppant+bubble-containing fracturing fluid), with a proppant concentration of 30%, and set it as Group C (the embodiment);

At the same time, prepare fracturing fluid with water-soluble hydrophobic viscosifier GAF-TP and foaming agent of the same concentration while injecting the same proportion of nitrogen into the fracturing fluid, stir and mix them well, and add the conventional quartz sand proppant (a unmodified quartz sand of 40-70 mesh provided by the same manufacturer) without surface hydrophobic modification at the same concentration of 30% to prepare 3 $m^3$ of proppant-carrying fracturing fluid, and define the modified fluid as Group D (Comparative Example 1);

Moreover, prepare fracturing fluid with water-soluble hydrophobic viscosifier GAF-TP of the same concentration (do not add the foaming agent) (the density of the fracturing fluid was tested to be 1.017 $g/cm^3$ and the viscosity was 6.57 mPa·s, without foaming effect; the density and viscosity were increased slightly), and add the conventional quartz sand proppant (a unmodified quartz sand of 40-70 mesh provided by the same manufacturer) without surface hydrophobic modification at the same concentration of 30% to prepare 3 $m^3$ of a conventional proppant-carrying fracturing fluid, and define the modified fluid as Group E (Comparative Example 2);

Test the proppant-carrying effect of Groups C, D and E with a large flat-plate proppant-carrying instrument respectively; the simulated fracture width of the instrument was 3 mm, and the pump speed of the proppant-carrying fluid during the test was 1.2 m³/min; the test results are shown in FIG. 12; It can be found from FIG. 12 that under the same conditions, the proppant-carrying effect of Group C in the embodiment was the highest, the proppant was displaced uniformly in both longitudinal and transverse directions and the light transmission of the proppant pack was higher, indicating that the proppant was more loosely packed and verifying the adsorption and aggregation effect between proppant and bubbles under the action of hydrophobic interaction; as for Groups D and E in comparative example, the proppant was unevenly distributed vertically and horizontally, and the light transmittance of the proppant pack was low, indicating that the proppant was settled significantly and densely packed; even if foaming agent and nitrogen at the same ratio were added to Group D, it was still difficult to effectively improve the proppant-carrying effect of the fracturing fluid without the application of hydrophobically surface-modified proppant;

Compare the actual proppant-carrying effects respectively of Group C in the embodiment and Groups D and E in the comparative example, and further confirm the effectiveness of the method discovered by the present invention in using hydrophobic proppant surface to adsorb bubbles to generate bubble bridge and form proppant-bubble aggregates, reducing the apparent density and thus achieving efficient proppant suspension and proppant-carrying effect. Moreover, this embodiment was conducted with 40 to 70-mesh quartz sand as proppant at normal temperature and pressure. However, the method of the present invention is also applicable to changing the proppant type (such as ceramsite), particle size, temperature and pressure.

In addition, what needs illustration is that, in the above embodiment, Step (3) of determining the Zeta potential of the hydrophobically surface-modified proppant under different pH conditions could be conducted after Step (7), and only the Zeta potentials at pH=5, 6, 7, 8 and 9, which were optimized for the first time, was determined.

The above embodiment presents only one specific application of the present invention which can also be used to determine the suspension parameters of the proppant by optimizing the salinity of base fluid, Zeta potential, bubble size, amount of treating agent added, volume of gas injected and so on.

The above are not intended to limit the present invention in any form. Although the present invention has been disclosed as above with embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. A method for proppant suspension parameter optimization based on bubble bridge effect, comprising the following steps:

Selecting a proppant and measuring its average particle size to obtain the average radius of the selected proppant;

Hydrophobically modifying the surface of the selected proppant to obtain a hydrophobically surface-modified proppant;

Preparing a water-based fracturing base fluid, injecting nitrogen into the base fluid, and stirring the base fluid to cause uniform bubbles to obtain a bubbly water-based fracturing base fluid;

Selecting a basic parameter of the bubbly water-based fracturing base fluid as a proppant suspension parameter for optimization, and preparing the bubbly water-based fracturing base fluid with different values of the basic parameter;

Measuring a Zeta potential of the bubbly water-based fracturing base fluid with different basic parameter values, and taking pictures of bubbles of each base fluid with a camera to obtain the average radius of the bubbles of each base fluid by image analysis;

Selecting a first optimization of the base fluids according to the average radius of the proppant and the average radii of the bubbles of the base fluids, wherein the first optimization includes calculating the ratio of the average radius of the proppant to the average radii of the bubbles of the base fluid; wherein the base fluids with a ratio in the range of 0.5-2 are the base fluids selected at the first optimization;

Preparing an electrolyte solution with the same pH as that of each base fluid selected at the first optimization, putting the hydrophobically surface-modified proppant into the electrolyte solution, and determining the Zeta potential of the hydrophobically surface-modified proppant in each electrolyte solution;

On the basis of the extended DLVO theory, calculating an interaction energy between the proppant particle and the bubble after the hydrophobically surface-modified proppant is mixed with the base fluids selected at the first optimization;

Optimally selecting the base fluids selected for a second optimization according to the interaction energy, wherein the second optimization comprises comparing the interaction energy of each base fluid, wherein the base fluids with relatively stronger hydrophobic attraction between the proppant particle and the bubble are the base fluids selected at the second optimization;

Putting the hydrophobically surface-modified proppant into each base fluid selected at the second optimization and strring them; wherein under the control of the interaction energy between the hydrophobic surface of the proppant and the bubble, the proppant particles are connected and aggregated through the bubble bridge effect into proppant-bubble aggregates; meanwhile, taking pictures of the proppant-bubble-proppant aggregation with the camera, determining a coefficient of bonding ratio between the proppant particle and the bubble through image observation and statistical analysis, and calculating an apparent density of the proppant-bubble aggregates; and Optimally selecting the base fluids selected for the third optimization according to the apparent density of proppant-bubble aggregates, wherein the third optimization comprises sorting out proppant-bubble aggregates with an apparent density in the range of 0.9-1.1 g/cm3; wherein the base fluids corresponding to the sorted-out proppant-bubble aggregates are the base fluids selected at the third optimization;

wherein the basic parameters of the bubbly fracturing base fluid selected at the third optimization are the optimized proppant suspension parameters.

2. The method for proppant suspension parameter optimization based on bubble bridge effect according to claim 1, wherein the proppant surface was hydrophobically modified by coating the proppant surface with an organic liquid suspending agent with hydrophobic effect.

3. The method for proppant suspension parameter optimization based on bubble bridge effect according to claim 1, wherein the basic parameter of the bubbly fracturing base fluid includes pH value, salinity, Zeta potential, bubble size, amount of treating agent added, or volume of gas injected.

4. The method for proppant suspension parameter optimization based on bubble bridge effect according to claim 1, wherein the interaction energy between the proppant particle and the bubble includes Van der Waals interaction energy, repulsive potential energy of the electric double layer, hydrophobic interaction force, and hydration repulsive force.

5. The method for proppant suspension parameter optimization based on bubble bridge effect according to claim 4, wherein the interaction energy between the proppant particle and the bubble is calculated by the following equation:

$$\Phi_T = \Phi_{LVD} + \Phi_{EDL} + \Phi_{HA} + \Phi_{HR} \tag{1}$$

Where, $\Phi_T$ is the interaction energy between the proppant particle and the bubble, in J; $\Phi_{LVD}$ is the Van der Waals interaction energy between the proppant particle and the bubble, in J; $\Phi_{EDL}$ is the repulsive potential energy of the electric double layer between the proppant particle and the bubble, in J; $\Phi_{HA}$ is the hydrophobic interaction force between the proppant particle and the bubble, in J; $\Phi_{HR}$ is the hydration repulsive force between the proppant particle and the bubble, in J;

Where, the Van der Waals interaction energy is calculated by the following equation:

$$\Phi_{LVD} = -\frac{A_{132}}{6D}\left(\frac{R_1 R_2}{R_1 + R_2}\right) \tag{2}$$

Where, $A_{132}$ is the Hamaker constant of the interaction between the proppant particle and the bubble in the base fluid, in J; D is the interaction distance between the proppant particle surface and the bubble surface, in m; $R_1$ and $R_2$ are the average values of proppant particles and bubbles, respectively, in m;

The repulsive potential energy of the electric double layer is calculated by the following equation:

$$\Phi_{EDL} = \pi\varepsilon_r\varepsilon_0 \frac{R_1 R_2}{R_1 + R_2}\left\{2\zeta_1\zeta_2\ln\left[\frac{1+\exp(-\kappa D)}{1-\exp(-\kappa D)}\right] + (\zeta_1^2 + \zeta_2^2)\ln[1-\exp(-2\kappa D)]\right\} \tag{3}$$

Where: $\varepsilon_r$ is the relative permittivity, taken as 81.5 for aqueous solution; $\varepsilon_0$ is the permittivity in vacuum, taken as $8.854 \times 10^{-12}$ $CV^{-1}m^{-1}$; $\zeta_1$ and $\zeta_2$ are the Zeta potentials of the proppant particle and the bubble, respectively, in V; $\kappa$ is the reciprocal value of the Debye length, in $m^{-1}$;

The hydrophobic interaction force is calculated by the following equation:

$$\Phi_{HA} = 2\pi \frac{R_1 R_2}{R_1 + R_2} h_{01} V_{HA}^0 \exp\left(-\frac{D}{h_{01}}\right) \tag{4}$$

Where, $h_{01}$ is the attenuation length of the hydrophobic interaction force, in m; V0 HA is the hydrophobic interaction energy constant between the proppant particle surface and the bubble, in $J/m^2$;

The hydration repulsive force is calculated by the following equation:

$$\Phi_{HR} = 2\pi \frac{R_1 R_2}{R_1 + R_2} h_{02} V_{HR}^0 \exp\left(-\frac{D}{h_{02}}\right) \tag{5}$$

Where, $h_{02}$ is the attenuation length of the hydration interaction force, in m; V0 HR is the hydration interaction energy constant between the proppant particle surface and the bubble, in $J/m^2$.

6. The method for proppant suspension parameter optimization based on bubble bridge effect according to claim 1, wherein the apparent density of the proppant-bubble aggregates was calculated by the following equation:

$$\rho_a = \frac{\rho_1 R_1^3 + k\rho_2 R_2^3}{R_1^3 + k R_2^3} \tag{6}$$

Where, $\rho_a$ is the apparent density of proppant-bubble aggregates, in $g/cm^3$; $\rho_1$ is the density of proppant particles, in $g/cm^3$; $R_1$ is the average radius of the proppant particles, in m; $\kappa$ is the coefficient of bonding ratio between the proppant particle and the bubble in aggregates, causeless; $\rho_2$ is the density of the bubbles, in $g/cm^3$; $R_2$ is the average radius of the bubbles, in m.

7. A method for proppant suspension based on bubble bridge effect, comprising the following steps:
Selecting a proppant and hydrophobically modifying its surface to obtain a hydrophobically surface-modified proppant;
Optimally selecting the suspension parameters of the proppant according to the methods for proppant suspension parameter optimization based on bubble ridge effect in claim 1;
Preparing a bubbly water-based fracturing base fluid based on the results of the proppant suspension parameter optimization; and
Mixing the hydrophobically surface-modified proppant with the bubbly fracturing base fluid to obtain a proppant suspension fracturing fluid that forms a gas-liquid-solid mixed system.

\* \* \* \* \*